(12) United States Patent
Kurachi et al.

(10) Patent No.: US 7,497,933 B2
(45) Date of Patent: Mar. 3, 2009

(54) GAS SENSOR

(75) Inventors: Hiroshi Kurachi, Aichi-gun (JP); Sang Jae Lee, Ama-gun (JP)

(73) Assignee: NGK Insulators, Ltd., Nagoya City (JP)

( * ) Notice: Subject to any disclaimer, the term of this patent is extended or adjusted under 35 U.S.C. 154(b) by 761 days.

(21) Appl. No.: 10/702,130

(22) Filed: Nov. 5, 2003

(65) Prior Publication Data
US 2004/0129564 A1 Jul. 8, 2004

(30) Foreign Application Priority Data
Nov. 12, 2002 (JP) ............................. 2002-327963

(51) Int. Cl.
*G01N 27/407* (2006.01)
(52) U.S. Cl. ..................... 204/427; 73/23.31
(58) Field of Classification Search ............... 204/424, 204/426, 427, 429; 73/23.31, 23.32
See application file for complete search history.

(56) References Cited

U.S. PATENT DOCUMENTS

| | | | |
|---|---|---|---|
| 4,282,080 A | 8/1981 | Müller et al. | |
| 4,283,441 A * | 8/1981 | Haecker et al. | ........... 427/126.2 |
| 4,559,126 A | 12/1985 | Mase et al. | |
| 4,909,922 A | 3/1990 | Kato et al. | |
| 6,350,357 B1 | 2/2002 | Wiedenmann et al. | |
| 6,666,962 B2 * | 12/2003 | Neumann et al. | ............ 204/427 |
| 2001/0047937 A1 | 12/2001 | Sugiyama et al. | |

FOREIGN PATENT DOCUMENTS

| | | |
|---|---|---|
| EP | 0 108 179 A1 | 5/1984 |
| JP | 02-001539 A1 | 1/1990 |
| JP | 09-318594 | 12/1997 |
| JP | 11-014594 A1 | 1/1999 |
| JP | 2000-025025 A1 | 1/2000 |
| JP | 2000-507359 A1 | 6/2000 |
| WO | WO 99/53302 A1 * | 10/1999 |

* cited by examiner

*Primary Examiner*—Kaj K Olsen
(74) *Attorney, Agent, or Firm*—Burr & Brown (57) ABSTRACT

The present invention provides a gas sensor which allows separation to hardly occur. A gas sensor 1 includes a gas detecting section 2 and a heater section 8 secured in the gas sensor, the heater section 8 including a heating element 3 and a support 9 which supports at least the heating element 3. An opening section 4 is provided to reduce pressure generated between the heating element 3 and the support 9.

12 Claims, 5 Drawing Sheets

GAS SENSOR

This application claims the benefit of Japanese Application 2002-327963, filed Nov. 12, 2002, the entirety of which is incorporated herein by reference.

BACKGROUND OF THE INVENTION

1. Field of the Invention

The present invention relates to a gas sensor for detecting the concentration of a gas such as oxygen, nitrogen oxide, sulfur oxide, carbon monoxide, or carbon dioxide contained in exhaust gas discharged from an internal combustion engine, a combustion furnace, or the like.

2. Description of Background Art

A gas sensor has been used to detect the concentration of a gas such as oxygen, nitrogen oxide, sulfur oxide, carbon monoxide, or carbon dioxide contained in exhaust gas discharged from an internal combustion engine such as an automotive engine, a combustion furnace, an incinerator, or the like. For example, the amount of air (oxidizing agent) or fuel to be supplied is controlled by measuring the concentration of a specific gas contained in the exhaust gas of the internal combustion engine so that the combustion state in the internal combustion engine is suitably controlled based on the detected signal. This prevents emission of incompletely combusted gas, allows exhaust gas to be purified, and reduces fuel consumption. It is preferable that such a gas sensor have a high degree of selective reactivity with the gas to be measured, be chemically stable against high-temperature exhaust gas, allow easy manufacture, and be reduced in size. Therefore, a gas sensor utilizing a solid sensor element, such as an oxygen sensor utilizing a solid electrolyte having oxygen ionic conductivity or a carbon monoxide sensor utilizing the semiconductor properties of tin oxide, has been widely used (see Japanese Patent Application Laid-open No. 9-318594, for example).

Such a gas sensor is generally operated in a predetermined high temperature region. Therefore, a gas sensor having a structure in which a heater is provided therein is widely used. However, there may be a case where separation occurs inside the gas sensor during use.

SUMMARY OF THE INVENTION

A feature of the present invention is to provide a gas sensor which can prevent separation.

The present invention provides A gas sensor which comprises: a gas detecting section; and a heater section secured in the gas sensor, the heater section including a heating element and a support which supports at least the heating element, wherein an opening section is provided to reduce pressure generated between the heating element and the support.

In the present invention, it is preferable that the opening section be provided so that at least a part of the support is exposed to an external atmosphere. It is still more preferable that the heater section include: the heating element; a lead electrically connected with the heating element; and the support which supports the heating element and the lead, wherein the opening section is provided so that at least a part of a section, or a vicinity thereof, of the support which supports the heating element is exposed to an external atmosphere. It is preferable that the heater section include the heating element; a lead electrically connected with the heating element; and the support which supports the heating element and the lead, wherein the opening section is provided so that at least a part of an interface between the heating element and the support or an interface between the lead and the support is exposed to an external atmosphere.

It is preferable that the gas detecting section include a solid electrolyte diaphragm; and at least a pair of electrodes, the one electrode being disposed on one surface of the diaphragm and the other electrode being disposed on another surface of the diaphragm. It is still more preferable that the solid electrolyte diaphragm include stabilized zirconia. It is preferable that the gas sensor include an air inlet space. It is still more preferable that the opening section open to the air inlet space.

DETAILED DESCRIPTION OF THE INVENTION AND PREFERRED EMBODIMENT

A gas sensor of the present invention is described below in detail based on specific embodiments. However, the present invention is not limited to the following embodiments.

Figure 1:
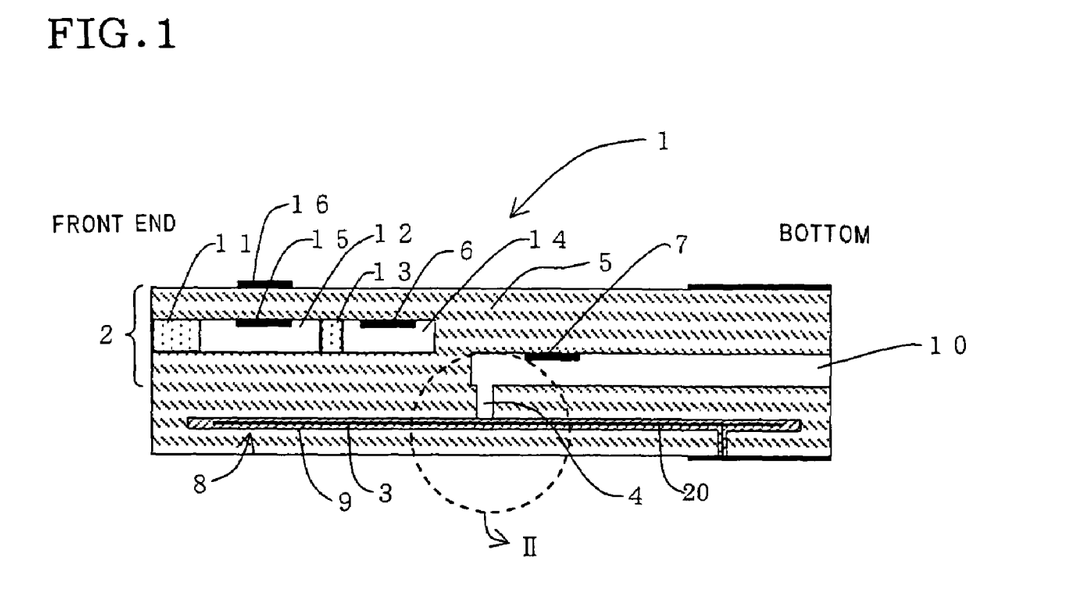
FIG. 1 is a schematic cross-sectional view showing an embodiment of a gas sensor according to the present invention.

FIG. 1 shows a $NO_x$ gas sensor as an example of the gas sensor of the present invention. A gas sensor 1 shown in FIG. 1 includes a gas detecting section 2, and a heater section 8 secured inside the gas sensor 1. The heater section 8 includes a heating element 3 and a support 9 which supports at least the heating element 3. An important feature of the present invention is that the gas sensor includes an opening section 4 which is provided to reduce pressure generated between the heating element 3 and the support 9.

A breakdown caused by separation which occurs near the heater in a conventional gas sensor has been examined in detail. As a result, it has found that separation occurs at the interface between the heating element and the support which supports the heating element (hereinafter referred to as "heating element interface"), and separation occurs at the heating element interface from the inside. It has found that separation which occurs near the heating element can be prevented by forming the opening section in the gas sensor 1.

The reason why occurrence of separation can be prevented by forming the opening section is considered to be as follows. Specifically, gaseous components such as air or components such as water present in the support which supports the heating element or present at the heating element interface expand due to heat generated by the heating element, thereby applying pressure which causes the heating element to be separated from the support. This is considered to be one cause of separation. Therefore, occurrence of separation can be prevented by forming the opening section so as to reduce pressure generated between the heating element and the support.

Figure 2:
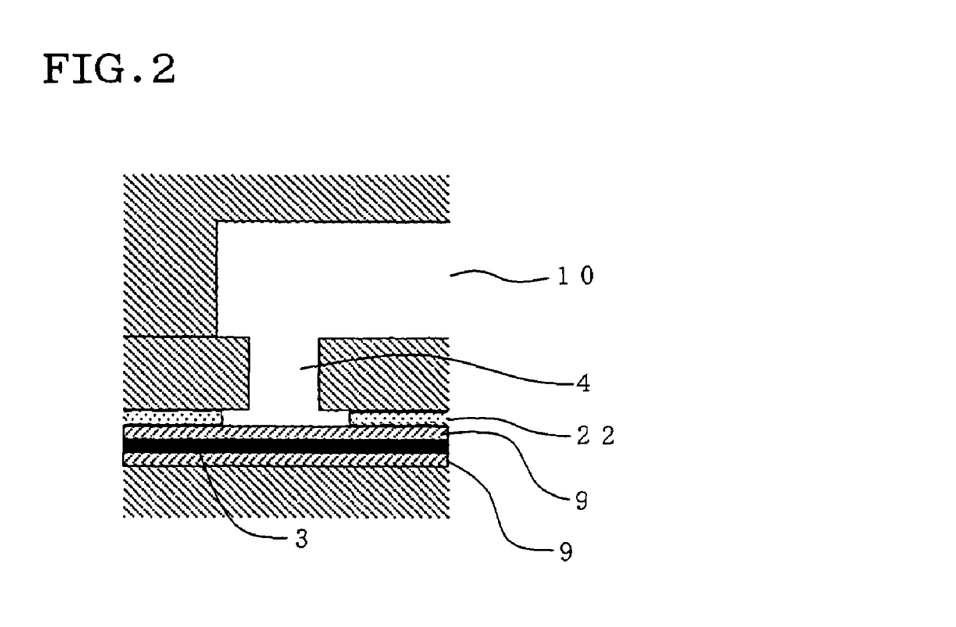
FIG. 2 is a schematic enlarged view of the section II shown in FIG. 1.
Figure 3:
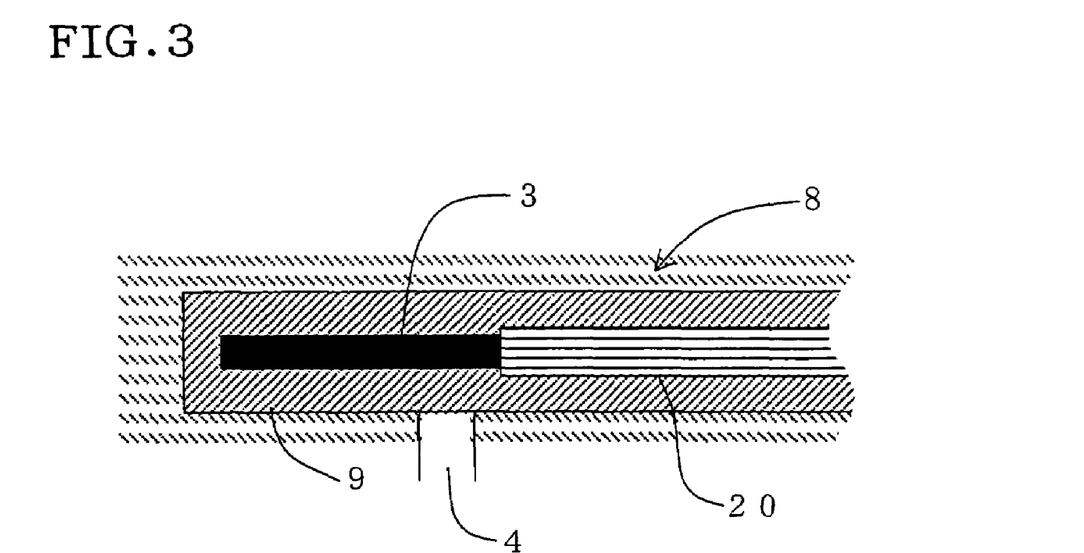
FIG. 3 is a schematic cross-sectional view showing an embodiment of a heater section and an opening section according to the present invention.

FIGS. 1 and 2 show an example of a specific embodiment of the opening section. In the embodiment shown in FIG. 1, the heater section 8 includes the heating element 3, a lead 20 which is electrically connected with the heating element 3, and the support 9 which supports the heating element 3 and the lead 20, as shown in FIG. 3. The opening section 4 is formed so that a part of the support 9 is exposed to an external atmosphere. This embodiment is preferably applied to the case where the support 9 is formed of a porous material. In order to effectively release the pressure, it is particularly preferable that the opening section 4 open to an external atmosphere from the surface of the section of the support which supports the heating element which rises in temperature.

Figure 4:
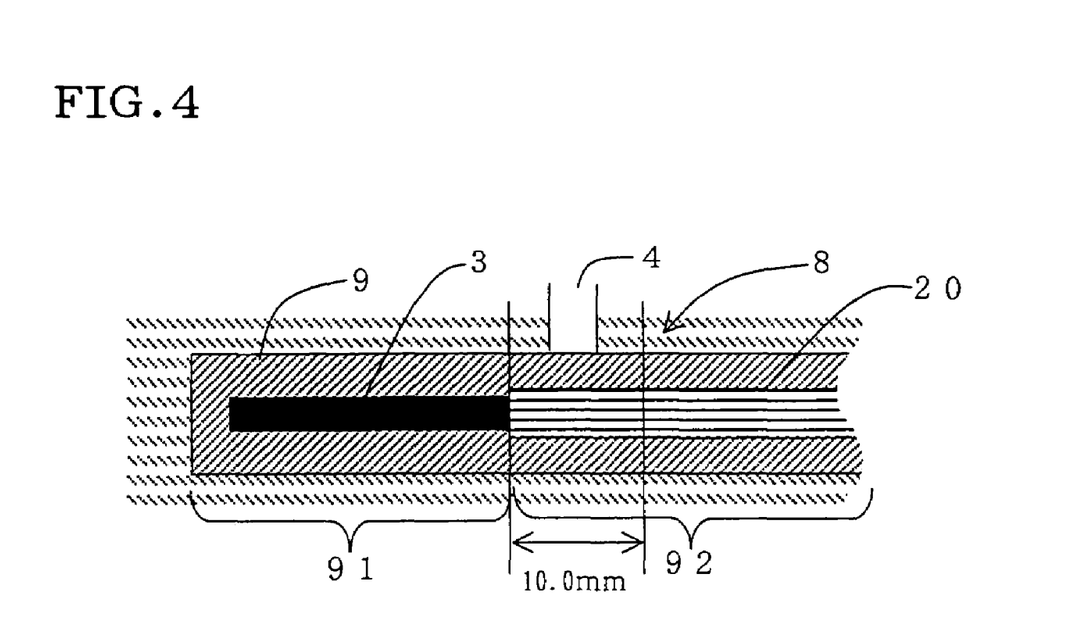
FIG. 4 is a schematic cross-sectional view showing another embodiment of a heater section and an opening section according to the present invention.

However, it suffices that the opening section in the present invention be formed to reduce the pressure generated between the heating element and the support insofar as the separation prevention effect of the present invention is achieved. Therefore, it is preferable that the opening section be formed so that an arbitrary section of the support is exposed to an external atmosphere. As shown in FIG. 4, the opening section 4 may be formed so that the section of the support 9 which supports the lead 20 is exposed to an external atmosphere.

In this case, if the location at which the support is exposed to an external atmosphere is an excessive distance from the heating element, the distance between the opening section and the section in which the pressure caused by expansion is maximum is excessively increased, whereby the separation prevention effect is reduced. Therefore, the location at which the support is exposed to an external atmosphere is preferably in the vicinity of the section which supports the heating element. The "vicinity of the section which supports the heating element" refers to a section at a distance of 10 mm or less, and preferably 5 mm or less from a section 91 of the support 9 which supports the heating element in the direction toward the section which does not support the heating element, such as a section 92 of the support 9 which supports the lead.

Figure 5:
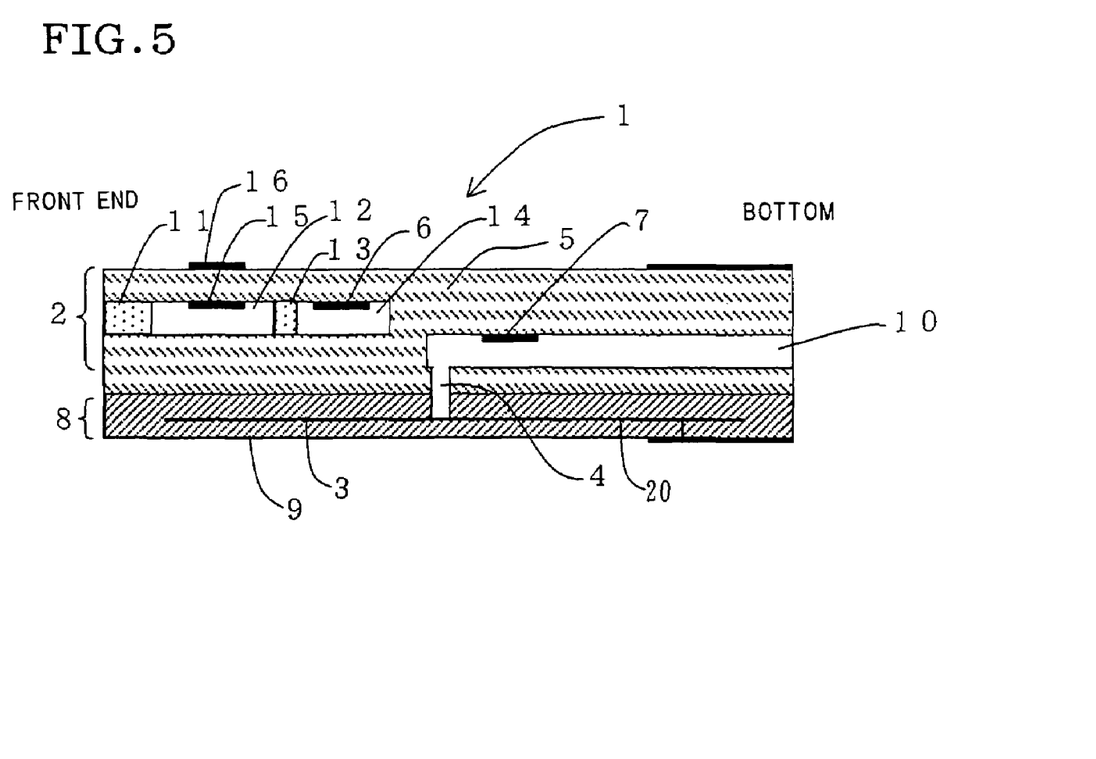
FIG. 5 is a schematic cross-sectional view showing another embodiment of a gas sensor according to the present invention.

FIG. 5 shows another embodiment of the opening section. In the sensor shown in FIG. 5, the opening section 4 is formed so that a part of the interface between the heating element 3 and the support 9 is exposed to an external atmosphere. This configuration is preferably applied to the case where the support is not porous. The pressure generated between the heating element and the support can also be reduced by allowing the opening section 4 to reach the interface between the heating element and the support, whereby separation can be prevented. In the embodiment shown in FIG. 5, the opening section 4 may be formed so that a part of the interface between the lead 20 and the support 9 is exposed to an external atmosphere. In this case, the opening section is preferably formed so that the interface between the section of the lead near the heating element and the support which supports this section is exposed to an external atmosphere.

The support used in the present invention supports and secures the heating element. The support may be porous or dense. It is preferable that the support be disposed to hold the heating element from both sides of the heating element. It is also preferable that the support be disposed to surround the entire heating element. It is also preferable that the support be disposed to integrally surround the heating element and the lead. It is also preferable that the support be formed of an insulator.

In the example shown in FIG. 1, a solid electrolyte diaphragm 5 and a first internal space 12 and a second internal space 14 which face the solid electrolyte diaphragm 5 are disposed in the gas detecting section 2 so that the first internal space 12 is located on the front end of the gas detecting section. An air inlet space 10 as a reference gas existence space is formed to extend in the longitudinal direction of the sensor element. A first diffusion controlling section 11 which introduces the gas to be measured into the first internal space 12 is formed on the front end of the gas detecting section. The first internal space 12 is connected with the second internal space 14 through a second diffusion controlling section 13.

An electrode 15 is formed on the section of the solid electrolyte diaphragm 5 which faces the first internal space 12, and an electrode 16 is formed on the external surface of the solid electrolyte diaphragm 5 corresponding to the electrode 15. An electrochemical pumping cell is formed by the electrodes 15 and 16 and the solid electrolyte diaphragm 5.

An electrode 6 is formed on the section of the solid electrolyte diaphragm 5 which faces the second internal space 14, and an electrode 7 is formed on the section of the solid electrolyte diaphragm 5 which faces the air inlet space 10. A pumping device for measurement is formed by the electrodes 6 and 7 and the solid electrolyte diaphragm 5.

The measurement mechanism of the $NO_x$ sensor having such a configuration is known in the art, and disclosed in Japanese Patent Application Laid-open No. 9-318594, for example. Japanese Patent Application Laid-open No. 9-318594 is incorporated herein by reference. In the sensor 1 shown in FIG. 1, the gas to be measured enters the first internal space 12 through the first diffusion-controlling section 11. The value of the diffusion-limited current of oxygen gas is calculated by applying a predetermined voltage between the pair of electrodes 15 and 16 provided on the inner and outer surfaces of the solid electrolyte diaphragm 5, facing each other. The $NO_x$ component which is not decomposed in the internal space 12 enters the second internal space 14 through the second diffusion controlling section 13. $NO_x$ is decomposed in the second internal space 14 by a voltage applied between the electrodes 6 and 7. $NO_x$ can be measured by calculating the amount of oxygen released in the accompanying decomposition.

There are no specific limitations to the configuration of the gas detecting section in the present invention. A detection section having various configurations may be used. It is preferable that the gas detecting section be solid. It is still more preferable that the gas detecting section include a solid electrolyte. It is particularly preferable that the gas detecting section include the solid electrolyte diaphragm 5, and the pair of electrodes 6 and 7 and/or 15 and 16. In each pair of electrodes, one electrode is disposed on one surface of the diaphragm 5 and the other electrode is disposed on the opposite surface of the diaphragm 5, as shown in FIG. 1. Since the gas detecting section having such a configuration is generally used in a predetermined high temperature region, separation tends to occur at the heating element interface due to an increase in temperature. Therefore, the configuration of the present invention is effective.

There are no specific limitations to the material for the solid electrolyte diaphragm insofar as the material generates electromotive force by the difference in partial pressure between gases to be measured. For example, a material having oxygen ionic conductivity is suitably used as the material for the solid electrolyte diaphragm. As examples of such a material, zirconium oxide, bismuth oxide, and cerium oxide can be given. Of these, stabilized zirconia excelling in high-temperature stability and chemical stability is suitably used. The stabilized zirconia refers to a material obtained by dissolving a divalent or trivalent metal oxide called a stabilizing material to cause the cubic crystal which is the high-temperature stable phase of zirconium oxide to be stable over a wide temperature range. The dissolution of the stabilizing material causes an oxygen defect to occur, thereby increasing ion conductivity. As the stabilizing material in the present invention, magnesium oxide (MgO), calcium oxide (CaO), yttrium oxide ($Y_2O_3$), cerium oxide ($CeO_2$), scandium oxide ($Sc_2O_3$), and rare-earth oxide are suitably used. The concentration of a gas such as nitrogen oxide or sulfur oxide can be measured by using the oxygen ion conductive solid electrolyte such as stabilized zirconia. The solid electrolyte diaphragm may be obtained by forming a formed product having a predetermined shape by using a conventional method, such as a press forming method, casting method, or a method of punching a green sheet obtained by an extrusion forming method or a doctor blade method, and debindering and firing the formed product.

The gas sensor of the present invention preferably includes the air inlet space 10, as shown in FIG. 1. Air can be used as the reference gas by providing such a space, whereby accurate measurement can be carried out.

Figure 6:
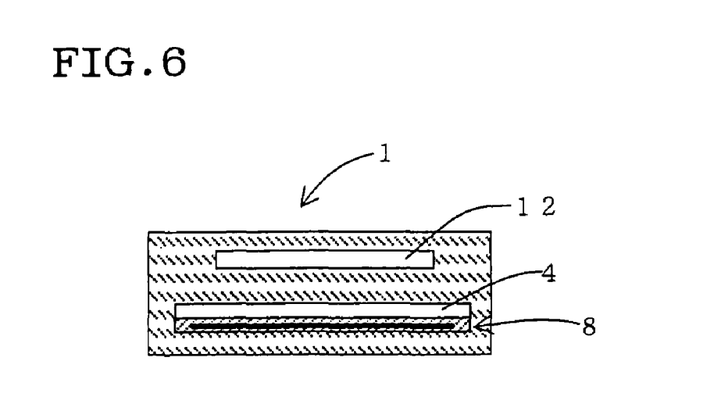
FIG. 6 is a schematic cross-sectional view showing yet another embodiment of a gas sensor according to the present invention.

There are no specific limitations to the opening position of the opening section 4 to the external atmosphere. The opening section 4 may open to the air inlet space as shown in FIG. 1, or open to the external atmosphere from any part of the gas sensor. The opening section may not be entirely hollow. A porous material may be disposed in the opening section 4, and the opening section may open to the external atmosphere through the porous material. The external atmosphere includes an atmosphere which contains the gas to be measured. The opening section may open to the atmosphere. There are no specific limitations to the shape of the opening section. The cross section of the opening section may be circular or polygonal. The opening section may open from the support in the vertical direction, oblique direction, or horizontal direction with respect to the support. FIG. 6 shows yet another embodiment of the opening section 4. As shown in FIG. 6, the opening section 4 may be formed by forming a groove or a space which opens to the external atmosphere along the heater section 8. There are no specific limitations to the size of the cross section of the opening section insofar as the effect of the present invention can be achieved. The size of the cross section of the opening section may be appropriately set depending on the size and shape of the gas sensor. In the case of a sensor formed by using a material having a shape shown in FIG. 7 or a sensor shown in FIG. 6, the effect of the present invention can be suitably achieved by setting the cross-sectional area of the opening section to preferably 0.01-240 $mm^2$, and still more preferably about 0.03-10.00 $mm^2$.

In the gas sensor of the present invention, there are no specific limitations to the shape and material for the heating element. It is preferable that the heating element generate a predetermined amount of heat by allowing a predetermined amount of current to flow through the heating element. There are no specific limitations to the material and shape of the support 9. The support 9 is preferably formed of a material such as alumina. The support 9 is preferably porous. In the gas sensor shown in FIG. 1, the heater section 8 is secured by using a heater adhesive layer 22 as shown in FIG. 2.

There are no specific limitations to the method of manufacturing the above-described gas sensor. For example, the gas sensor may be manufactured by laminating sheets containing ceramics. Since separation easily occurs at the heating element interface in a laminated type gas sensor manufactured in this manner, the present invention can be particularly effectively applied.

Figure 7:
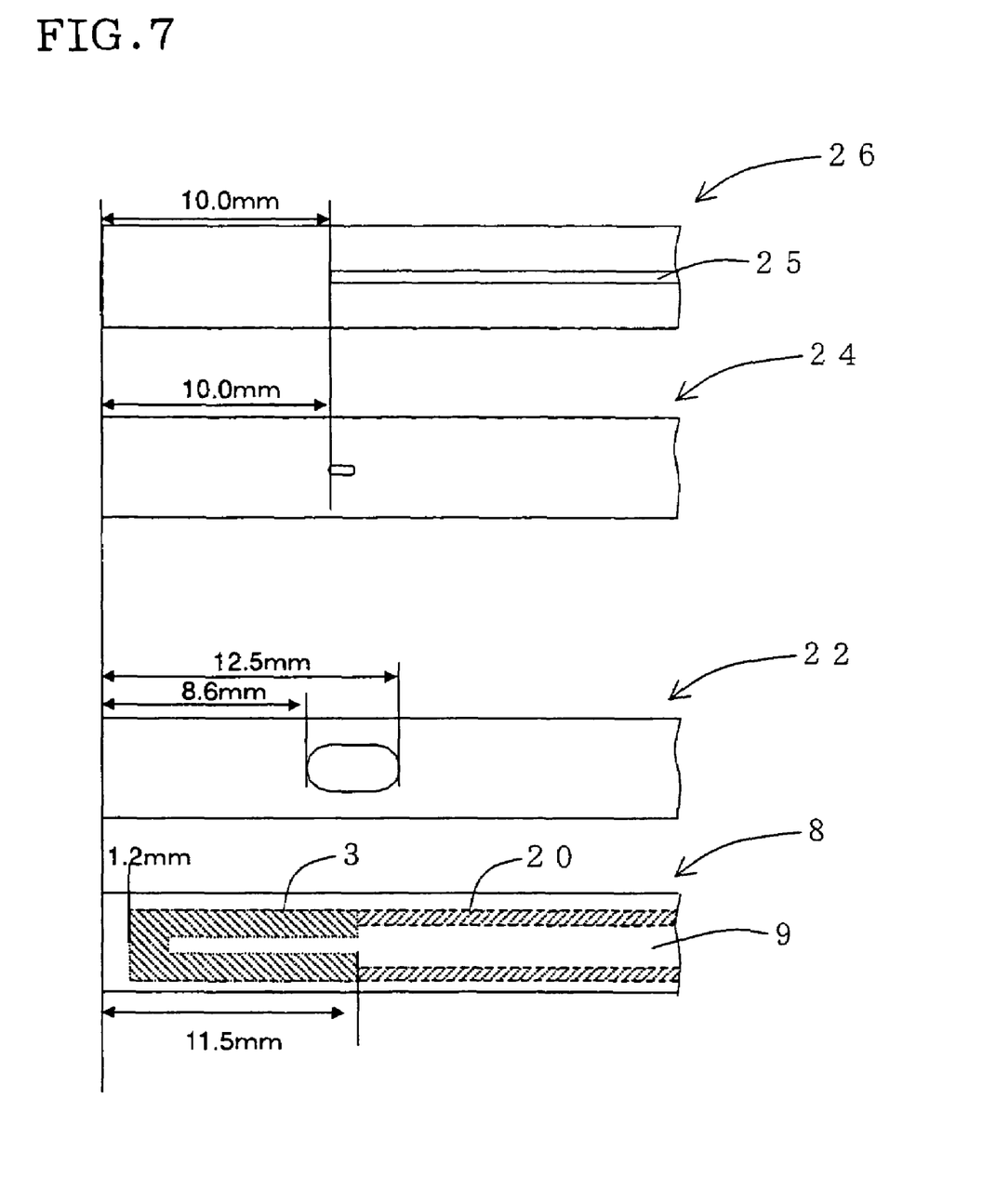
FIG. 7 is a view schematically showing a method of forming an opening section according to the present invention.
Figure 8:
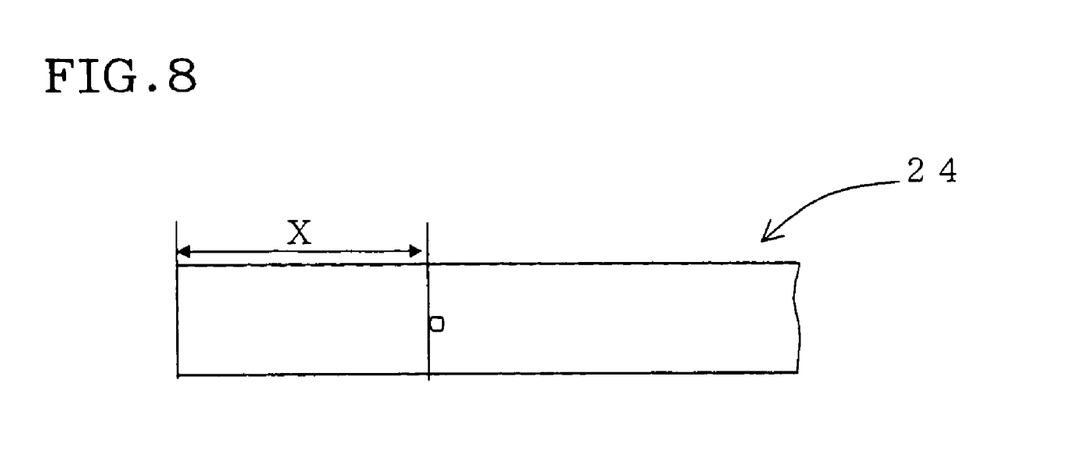
FIG. 8 is a view schematically showing the location of an opening section according to the present invention.

There are no specific limitations to the method of forming the opening section of the present invention. For example, the opening section may be formed by using the following method. In the case of manufacturing the $NO_x$ sensor shown in FIG. 1 by laminating sheets containing stabilized zirconia, holes are formed in the heater adhesive layer 22 and a first stabilized zirconia layer 24 as shown in FIG. 7. The opening section may be formed by laminating in the order of: the heater section 8 consisting of the heating element 3, the lead 20, and the alumina support 9; the heater adhesive layer 22; and a second stabilized zirconia layer 26 having a groove 25 for forming the air inlet space.

There are no specific limitations to the application of the gas sensor of the present invention. When it is used in a vehicle, there may be a case where an excessive voltage called load dump, which occurs at the time of turning an alternator (generator) ON or OFF, is applied to the heater section of the gas sensor. In this case, the heating element may generate an excessive amount of heat, and an excessive amount of force may be applied between the heating element and the support which supports the heating element. The opening section also functions effectively in this case. In the case of installing the gas sensor in a vehicle, the gas sensor may be installed in an exhaust pipe so that the gas detecting section comes in contact with the atmosphere inside the exhaust pipe of the vehicle.

EXAMPLES

The present invention is described below in more detail based on examples. However, the present invention is not limited to the following examples.

Examples 1-3

Holes were formed in the heater adhesive layer 22 and the first stabilized zirconia layer 24, as shown in FIG. 7. The heater section 8 and the second stabilized zirconia layer 26 were laminated on the heater adhesive layer 22 and the first stabilized zirconia layer 24. Other layers were further laminated so that the structure shown in FIG. 1 was obtained, to provide a gas sensor having the structure shown in FIG. 1. The area of the hole formed in the first stabilized zirconia 24 was 0.13 $mm^2$. Each distance X between the hole and the front end of the gas sensor was 10.0 mm, 11.0 mm, and 12.0 mm for the examples 1, 2, and 3, respectively.

Comparative Example 1

A gas sensor was obtained in the same manner as in the example 1 except that holes were not formed in the heater adhesive layer and the first stabilized zirconia layer.

(Measurement of Breakdown Voltage)

The bottom section of the gas sensors obtained in the examples 1-3 and the comparative example 1, that is, the section opposite to the front end section in which the gas detecting section was formed, was immersed in water for four hours. After removing water adhering to the surface, a voltage of 6 V was applied to the heater section of the gas sensor. The voltage was increased to 12 V in units of 1 V to examine the breakdown voltage of gas sensor by separation in the heater section. The measurements were made on three specimens for the gas sensors of the examples 1 and 2, five specimens for the gas sensor of the example 3, and 15 specimens for the gas sensor of the comparative example 1.

The results are shown in Table 1. Breakdown of all the specimens of the comparative example 1 occurred at an applied voltage of 6-8 V due to separation. On the contrary, separation only occurred in the specimens of the examples 1-3 at an applied voltage 10 V or more. This shows that separation rarely occurs in the gas sensor of the present invention. Specifically, breakdown of the gas sensor of the present invention was hard to occur. The specimens of the example 1 had the highest breakdown voltage. The breakdown voltage decreased to a small extent in the order of the examples 2 and 3. In the specimens of the example 1, the opening section was formed on the section of the support which supports the heating element. In the specimens of the example 3, the opening section was formed on the section of the support which supports the lead, that is, at a location at a small interval from the section of the support which supports the heating element. Therefore, the specimens of the example 1 in which the opening section was formed so that the section of the support which supports the heating element was exposed to the external atmosphere showed better results. However, a sufficient improvement effect was obtained in the example 3 in which the opening section was formed so that the section of the support near the heating element was exposed to the external atmosphere, even if the section of the support which supports the heating element was not directly exposed to the external atmosphere.

Examples 4-6

Figure 9:
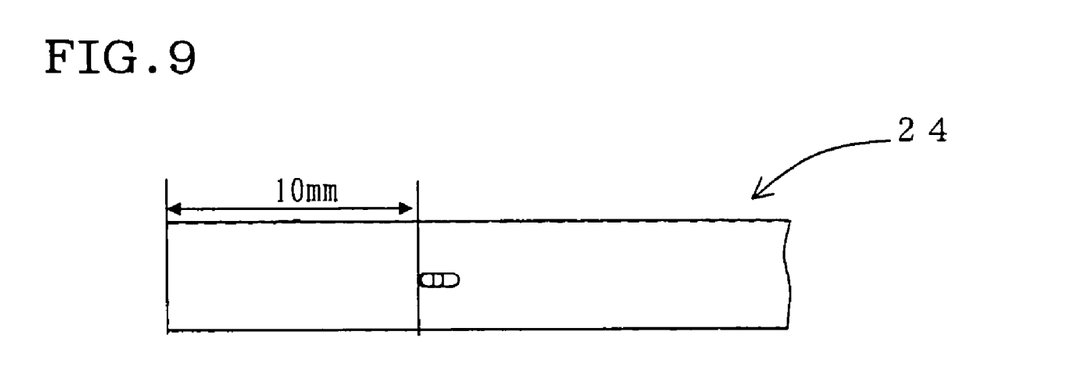
FIG. 9 is a view schematically showing the location and size of an opening section according to the present invention.

As shown in FIG. 9, gas sensors were obtained in the same manner as in the example 1 except that the distance between the hole and the front end of the gas sensor was fixed at 10.0 mm and the area of each hole was 0.13 mm, 0.25 mm, and 0.38 mm for the examples 4, 5, and 6, respectively. The breakdown voltage was measured in the same manner as in the example 1. The specimens of the example 4 had the same shape as the shape of the specimens of the example 1.

The results are shown in Table 1. The specimens of the examples 4-6 showed extremely good results, in which breakdown due to separation did not occur even at an applied voltage of 12 V.

What is claimed is:

1. A gas sensor which comprises:
   a gas detecting section;
   a heater section secured in the gas sensor, the heater section including a heating element sandwiched between two porous layers that define a support which supports at least the heating element;
   a reference gas space extending along a longitudinal direction of the gas sensor; and
   an opening section extending through and being completely surrounded by at least one layer of the gas sensor, the opening section extending substantially perpendicular to the reference gas space to provide communication between the reference gas space and the heater section so as to reduce pressure generated between the heating element and the support, wherein the opening section is provided so that at least a part of the support is exposed to an external atmosphere.

2. The gas sensor according to claim 1, wherein the heater section includes:
   the heating element;
   a lead electrically connected with the heating element; and
   the support which supports the heating element and the lead,
   wherein the opening section is provided so that at least a part of an interface between the heating element and the support or an interface between the lead and the support is exposed to an external atmosphere.

3. The gas sensor according to claim 2, wherein the gas detecting section includes:
   a solid electrolyte diaphragm; and
   at least a pair of electrodes, the one electrode being disposed on one surface of the diaphragm and the other electrode being disposed on another surface of the diaphragm.

4. The gas sensor according to claim 3, wherein the solid electrolyte diaphragm includes stabilized zirconia.

5. The gas sensor according to claim 2, which comprises an air inlet space.

6. The gas sensor according to claim 5, wherein the opening section opens to the air inlet space.

TABLE 1

| | Distance between opening section and front end = X (mm) | Cross-sectional area of opening section (mm$^2$) | Number of specimens | Number of specimens broken down Applied voltage (V) | | | | | | | |
|---|---|---|---|---|---|---|---|---|---|---|---|
| | | | | 5 | 6 | 7 | 8 | 9 | 10 | 11 | 12 |
| Example 1 | 10.0 | 0.13 | 3 | 0 | 0 | 0 | 0 | 0 | 0 | 0 | 3 |
| Example 2 | 11.0 | 0.13 | 3 | 0 | 0 | 0 | 0 | 0 | 0 | 2 | 1 |
| Example 3 | 12.0 | 0.13 | 5 | 0 | 0 | 0 | 0 | 0 | 3 | 2 | — |
| Example 4 | 10.0 | 0.13 | 3 | 0 | 0 | 0 | 0 | 0 | 0 | 0 | 0 |
| Example 5 | 10.0 | 0.25 | 3 | 0 | 0 | 0 | 0 | 0 | 0 | 0 | 0 |
| Example 6 | 10.0 | 0.38 | 3 | 0 | 0 | 0 | 0 | 0 | 0 | 0 | 0 |
| Comparative Example 1 | — | — | 15 | 0 | 5 | 9 | 1 | — | — | — | — |

As described above, the gas sensor of the present invention can be hard to break down due to separation in the heater section. Therefore, the gas sensor of the present invention can be suitably used to detect the concentration of a gas such as oxygen, nitrogen oxide, sulfur oxide, carbon monoxide, or carbon dioxide contained in exhaust gas discharged from an internal combustion engine such as an automotive engine, a combustion furnace, an incinerator, or the like.

7. The gas sensor according to claim 1, wherein the gas detecting section includes:
   a solid electrolyte diaphragm; and
   at least a pair of electrodes, the one electrode being disposed on one surface of the diaphragm and the other electrode being disposed on another surface of the diaphragm.

8. The gas sensor according to claim 7, wherein the solid electrolyte diaphragm includes stabilized zirconia.

9. The gas sensor according to claim 1, which comprises an air inlet space.

10. The gas sensor according to claim 9, wherein the opening section opens to the air inlet space.

11. The gas sensor according to claim 1, wherein an area of the opening section is 10 mm² or less.

12. The gas sensor according to claim 1, wherein a distance, d, from a front end of the gas sensor to the opening section satisfies the following inequality:

$$10 \text{ mm} \leq d \leq 12 \text{ mm}.$$

* * * * *